(12) United States Patent
Hansen

(10) Patent No.: US 6,290,980 B1
(45) Date of Patent: Sep. 18, 2001

(54) PACKAGING AND METHOD FOR SOLID DOSE ADMINISTRATION OF MEDICAMENTS

(75) Inventor: Richard D. Hansen, Urbandale, IA (US)

(73) Assignee: Solidose, LLC, Oklahoma City, OK (US)

( * ) Notice: Subject to any disclaimer, the term of this patent is extended or adjusted under 35 U.S.C. 154(b) by 0 days.

(21) Appl. No.: 09/560,213

(22) Filed: Apr. 28, 2000

(51) Int. Cl.[7] .................................................. A61F 13/00
(52) U.S. Cl. .................... 424/422; 424/400; 424/405; 424/408; 424/438; 424/489; 604/48; 604/500; 604/502; 604/57; 604/59
(58) Field of Search .................... 424/400, 405, 424/422, 408, 438, 489; 604/48, 500, 502, 57, 59

(56) References Cited

U.S. PATENT DOCUMENTS 5,665,363   9/1997  Hansen et al. ..................... 424/211.1
5,874,098 * 2/1999  Stevens et al. ...................... 424/408

* cited by examiner

Primary Examiner—Thurman K. Page
Assistant Examiner—Charesse L. Evans
(74) Attorney, Agent, or Firm—Zarley, McKee, Thomte, Voorhees & Sease

(57) ABSTRACT

A method and packaging for vaccinating or medicating an animal by implanting a solid dose medicament in an animal. The solid dose medicament, or plurality of such medicaments, are each color-coded to identify a particular active ingredient, then packaged in a pellet magazine through which the doses are visible, and thereafter the pellets are implanted, usually subcutaneously, into the base of the ear or in the neck of an animal. The same system can be used for colored ballistic implants.

14 Claims, 2 Drawing Sheets

PACKAGING AND METHOD FOR SOLID DOSE ADMINISTRATION OF MEDICAMENTS

FIELD OF THE INVENTION

This invention relates to inoculation of living animals, usually livestock or wildlife, with biologically active solid dose pellets. They may be administered subcutaneously as implants, or ballistically as a projectile.

BACKGROUND OF THE INVENTION

Pellet implant systems which administer hormonal medicaments subcutaneously are known. Typically, they use a dosing gun to administer a series of pharmaceutical pellet implants, usually to the ear of an animal to provide sustained release of medicament. A dosing gun or implanter usually incorporates pellet magazines containing multiple doses of pharmaceutical pellets which are inserted subcutaneously into the ear tissue with an associated injection needle. The magazine channels are loaded with a series of identical pharmaceutical pellets for administration at the same injection site.

Implant technology, that is to say, procedures involving subcutaneous implants of pharmaceuticals and medical devices, are now well accepted and widespread in the areas of animal health and production enhancement. Growth stimulants are commonly used to enhance the body weight of animals which are raised for slaughtering, such as cattle, swine, sheep, turkeys, chickens and the like. A medicament in the pellet is normally formulated for continuous sustained absorption of the active ingredients over an extended period of time.

Solid dose ballistic projectiles shaped for penetrating the epidermal layer of living animal tissue are also known. These are typically fired remotely, using an airgun. They lodge totally within the tissues of the animal for later release of biologically-active medicaments into the animal tissue. They have an advantage over typical hand-held implant apparatus using a needle in that the inoculated animal need not be "captured".

This invention may be used with either type of solid dose administration, but has been found particularly useful with hand-held implant administration, more particularly where combined dosing of a plurality of biologically active materials is achieved with a single needle-inserted, subcutaneous implantation. For details of such implant systems, see my previous patent, U.S. Pat. No. 5,665,363, issued Sep. 9, 1997, and as well, other prior patents on pellet implant systems, such as U.S. Pat. No. 5,874,098, issued Feb. 23, 1999. Disclosures of each of these are incorporated herein by reference.

Particularly, when animals are multiply dosed, it is necessary for the medicament administrator to keep track of medicaments, and of which animals have in fact been dosed. This can be particularly bothersome when multiple dosing of a medicament occurs with a single subcutaneous implant, or shot, in the case of a ballistic implant. This invention has as its objective a new method, packaging and system for keeping track of and systematically administering a plurality of medicaments to animals so that the operator, or medicament administrator, can be confident that all desired medicaments have in fact been administered.

SUMMARY OF THE INVENTION

A method and packaging for vaccinating or medicating an animal by implanting a solid dose medicament in an animal. The solid dose medicament, or plurality of such medicaments, are each color-coded to identify a particular active ingredient, then packaged in a pellet magazine through which the doses are visible, and thereafter the pellets are implanted, usually subcutaneously into the base of the ear or in the neck of an animal. The same system can be used for colored implants administered ballistically.

DESCRIPTION OF THE PREFERRED EMBODIMENT

While the description here is given as a preferred embodiment of the invention, it is to be understood that the invention is not limited to preferred embodiment. Rather, the invention is limited only by the defining limits of the claims, as opposed to any statements in the specification relating to the preferred embodiment.

Figure 1:
FIG. 1 is a front view of a bovine head, showing the ears.
Figure 2:
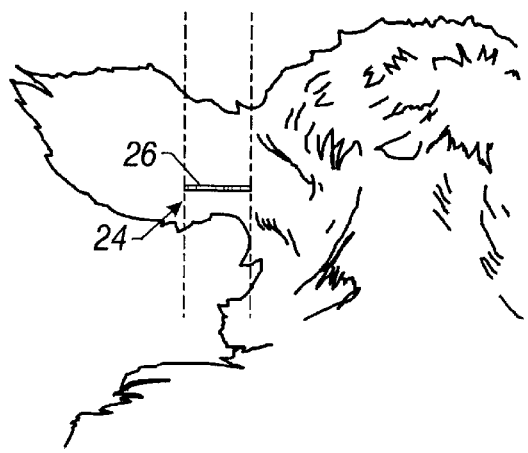
FIG. 2 is a back view of a bovine head for illustrative purposes, showing the subcutaneous biological ear implant site.

A calf 10 is indicated for illustrative purposes of showing the working of the medicament implant system. A suitable solid dosing implanter 12 of known construction can be used. Such devices generally include a housing 14 with a pistol grip 16, a trigger 18, and a subcutaneous implant needle. The pellet implant magazine 22 is inserted into the implanter apparatus 12, and moves downwardly therethrough as trigger 18 is pulled, unloading its biological or pharmaceutical dose through a needle as trigger 18 is pulled. This action forces the multiple doses through the bore of the needle (not depicted) attached to the implant apparatus 12, and into a subcutaneous puncture, particularly in the base of the ear 24 as illustrated at 26, FIG. 2, or in the neck. For details of such a method, see my earlier U.S. Pat. No. 5,665,363.

Figure 3:
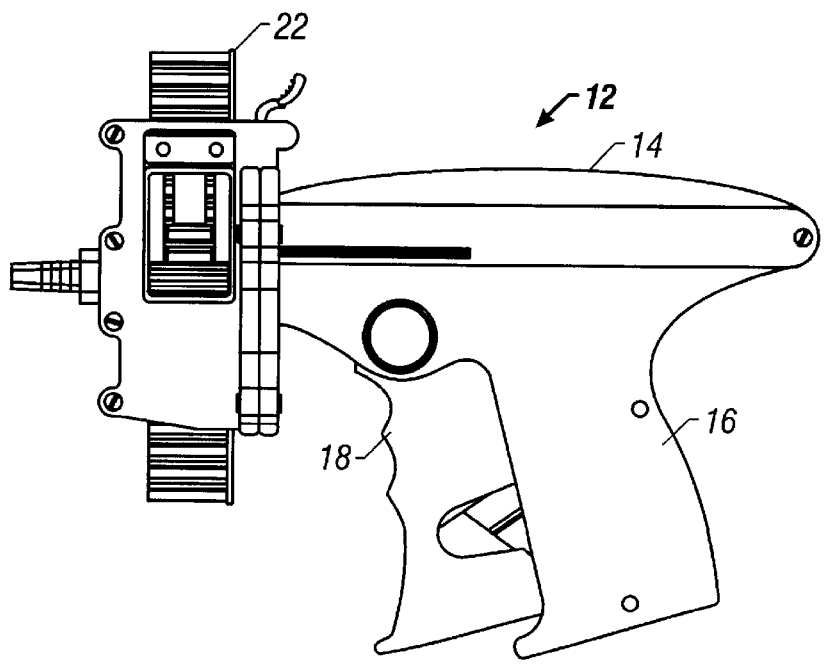
FIG. 3 is a side view of a solid dosing implanter.
Figure 4:
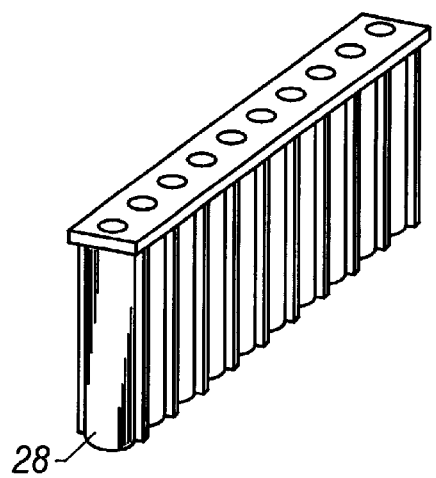
FIG. 4 shows a typical pellet magazine in perspective.

Pellet magazine 22 is illustrated in perspective in FIG. 4 and in FIG. 3 as it would enter from the top and exit below the implanter apparatus 12. It can be seen that pellet magazine is made of an inert, see-through polymeric plastic material. The magazine 22 used with implanter 12 typically contains multiple, parallel-aligned, pellet dosing columns or chambers 28. As illustrated, the chambers are generally of such a construction that each has a hollow internal core. The chambers 28 are in side-by-side parallel relation, as illustrated.

Figure 5:
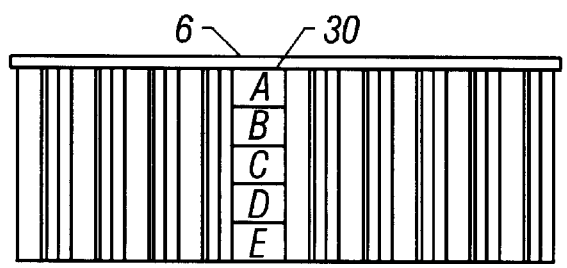
FIG. 5 shows a pellet magazine which is transparent, showing how the pellets are arranged in a prearranged multiple dosing order.
Figure 6:
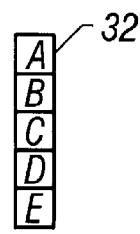
FIG. 6 shows how the prearranged dosing order for the pellets can be color-coded.

Each chamber 28 is loaded with a plurality of discrete dosing pellets in columnar relationship, as illustrated in FIG. 5 at 30. Individual pellets in similar stacked relationship are shown in FIG. 6. The individual pellets 32 are composed of an identified biologically active ingredient in conjunction with one or more excipients formed as part of a polymeric base release system such as described in my earlier U.S. Pat.

No. 5,665,363. Each of the solid dose pellets 32 include a wide range of biologically active medicaments. Indeed, the particular medicament used for pellet 32 is not a limitation on the invention. For example, the medicaments may be hormones, minerals, vitamins, antibiotics, antigens, antibodies, tranquilizers, dewormers, etc.

Preferably, the biologically active pellet comprises about 2% to 70% by weight of a medicament. More preferably, the biologically active pellet comprises about 3% to 50% by weight of the medicament, most preferably about 4% to 20% by weight.

Typically, the dried powder mixture is blended with a lubricant and pelletized into final form. Lubricants facilitate the release of the pellets from the pelleting dies.

A list of lubricants that can be used in the practice of the invention includes, but should not be limited to, magnesium stearate, calcium stearate, sodium stearyl fumarate, stearic acid, sodium lauryl sulfonate, polyoxyethylene (carbowaxes), polyethylene glycols, glycerol behenate, hydrogenated vegetable oils and mixtures thereof. Preferably, the lubricant contains calcium stearate.

Generally, the biologically active pellet comprises an effective pellet-forming amount of a lubricant. Preferably, the biologically active pellet comprises about 0.2% to 5% by weight of a lubricant. More preferably, the biologically active pellet comprises about 0.5% to 3.5% by weight of a lubricant, most preferably about 1.0% to 2% by weight.

TABLE 1

| | % By Weight of the Biologically Active Pellet | | |
|---|---|---|---|
| | Working Range | Preferred Range | Most Preferred Range |
| Biologically Active Material | 2%–70% | 3%–50% | 4%–20% |
| Excipients | balance | balance | balance |
| Lubricant | 0.2%–5% | 0.5%–3.5% | 1%–2% |

Optionally, the biologically active pellet can comprise additional excipients. These additional excipients can be added to the biologically active pellet to provide increased strength, to control dissolution rates, to improve powder handling, e.g., flow and the like, or to improve the efficacy of the product. A list of additional excipients that can be used as the biologically active pellet of the invention includes, but should not be limited to: precipitated or fumed silicas, sodium starch glycolates, calcium phosphate, calcium carbonate, dextrins, polyvinyl pyrrolidone, hydroxypropylcellulose, hydroxypropylmethylcellulose, polylactic acid, polyglycolic acid, magnesium aluminum silicates, microcrystalline cellulose, sodium carboxymethylcellulose and mixtures thereof. Preferably, these additional excipients are less than about 50% by weight of the biologically active pellet. More preferably, these additional excipients constitute less than about 40% by weight of the biologically active pellet, most preferably 25% by weight.

Pellets may be generally prepared as follows:

A liquid suspension containing, for example, bacterial cells and associated products adsorbed on aluminum hydroxide gel is mixed with sufficient mannitol to yield a final weight of 15 milligrams per dose of product. The suspension is dispensed into containers, frozen, and the water removed under vacuum. After freeze drying is complete, the dried powder is harvested. The powder is processed to reduce the particle size to less than 0.1 millimeter, and sufficient calcium stearate (approximately 1% by weight) is added for lubrication.

The powder blend is then tabletted on a conventional tableting machine to produce uniform pellets. A typical formulation for the above pellets would be:

| | |
|---|---|
| Freeze-dried powder | 15 |
| Calcium stearate | 2 |
| Precipitated silica | 0.5 |
| Filler, | balance |

(Powder has 10 parts bacterial antigen and 5 parts mannitol)

Pellets produced as above may, if desired, be converted to delayed release pellets by coating with materials that will delay the escape of the medicament to the body. Materials that are useful for this are compounds that will slowly degrade or dissolve in the body fluids. Examples of materials suitable for use are hydrolytically unstable polymers such as polylactic acid, polymers such as ethylvinyl acetate that are slow to dissolve in body fluids, or waxy solids, such as cholesterol, that have a limited solubility in aqueous fluids. These materials can be applied to the tablet as coatings and will act to delay the release of the active ingredient from the pellet.

There are a number of coating techniques available for adding the delayed release coatings to the pellets. Rotating drum coaters or fluidized bed coating processes can be used. Any process that can apply a uniform coating in a controlled manner can be used. The thickness of the coating and water solubility will determine the delay before the product is released.

The biologically active pellets of the invention can be formed into any possible shape that the pelletizing machine is capable of making. Preferably, the shape and size of the biologically active pellet is one suitable for implanting into the animal. More preferably, the shape of the biologically active pellet is such that it can be used in conjunction with an implant gun. Most preferably, the shape and size of the pellet is adapted for implanting the biologically active pellet subcutaneously into an ear or neck of the animal.

In general, the size of the biologically active pellet depends on the dose to be administered to the animal and compatibility with the implant gun and needle used.

The biologically active pellets of the invention can be implanted into any animal which is capable of responding to the biologically active material. Generally, these animals include, but should not be limited to, cattle, hogs, horses, cats, dogs, sheep, goats, for example. In a preferred embodiment of the invention, the animal is domestic cattle.

The biologically active pellet can be subcutaneously implanted into any area of the animal which allows the biologically active pellet to come into contact with tissue fluids. Preferably, the biologically active pellet is implanted into an area of the animal which minimizes or eliminates lasting damage to edible tissue of the animal. More preferably, the biologically active pellet is implanted into an ear, the neck, the tail-head or flank areas of the animal, thereby reducing potential damage to edible tissue. Most preferably, the biologically active pellet is implanted into the ear of cattle, thereby eliminating damage to edible tissue.

In our earlier patent, I found that implanting the biologically active pellet into an ear of the animal does not result in an undesirable "drooped ear", or "down ear" in the animal. As with any product administered through the skin, sanitary methods must be followed to reduce the likelihood of injection site infections/abscesses which may result in undesirable local tissue reactions.

The plurality of medicaments, if used, may be arranged in any predetermined order. One may arbitrarily select colors to represent each medicament pellet in the stack. For example, one vaccine could be represented by yellow, a second vaccine by blue, a third vaccine by white, a bacterin by green, and a second bacterin by red. These would be stacked in the order shown in FIG. 6 so that looking through the columns 30 in FIG. 5 one would see in this order from top to bottom yellow, blue, white, green, red. In all customer literature accompanying the dosing pellet magazine 28, the same color scheme would be consistently used throughout the description which accompanies the medicaments.

While the description herein has been given particularly with hand-held implant dosing, ballistic implants can be used of the type disclosed in my co-pending application simultaneously filed herewith entitled "MEDICAMENT DOSING BALLISTIC IMPLANT OF IMPROVED ACCURACY", Ser. No. 09/561,224. If a similar color scheme is used with various medicaments, the implant casing itself could incorporate the color scheme as opposed to the payload. In like manner, the packaging could use consistent representations with regard to color being coordinated with specific medicaments. Such a ballistic implant would usually only contain a single medicament. Thus, for example, if an implant casing were yellow, one would know it contained a certain vaccine; if it were blue, one would know it contained another vaccine; red a certain bacterin; and so forth.

Use of the colorants is nonlimiting, but generally they would include FD&C colorants known to be non-harmful to the animals to be vaccinated, substantially inert to the administered biologically active material, and leave no persistent tissue discoloration.

The following were tested and found "non-viricidal" to the principal cattle modified live viruses (MLV) one might include in cattle vaccines. These include: Infectious Bovine Rhinotracheitis (IBR) Virus, Bovine Virus Diarrhea (BVD) Virus, Parainfluenza 3 (PI-3) Virus and Bovine Respiratory Syncytial Virus (BRSV): FD&C Red #40 aluminum lake pigment, FD&C Blue #1 aluminum lake pigment, FD&C Yellow #5 aluminum lake pigment.

These pigments in pellets were also found to leave no visible residues in the subcutaneous tissue of rabbits. Pellets containing FD&C Red #40 left no visible residues in cattle. FD&C Blue #1 and FD&C Yellow #5 have not been tested in cattle to date.

The FD&C Red #40 was accepted as satisfactory by the USDA-CVB (Center for Veterinary Biologics) and the FSIS (Food Safety and Inspection Service). Application will be made shortly to the CVB for acceptance of FD&C Blue #1 and FD&C Yellow #5 based on the data gathered.

It is likely the above actually tested list could be expanded to include other 21 CFR listed FD&C and D&C aluminum lake pigments, as well as other colorants (e.g., iron oxides, phenol red). Those next likely candidates include: FD&C Yellow #6 aluminum lake pigment, FD&C Red #40Y, FD&C Blue #2.

Color candidates may also be used in combination to create other colors (e.g., green).

The list of medicaments includes only veterinary products approved to be administered by the parenteral route. Generally, the products could include antigens related to: Vaccines (Live or Killed Virus), Bacterins and Bacterial Extracts (Killed organisms), Bacterin-Toxoids (Killed organisms+modified toxins), Toxoids (Modified toxins devoid of killed bacterial cells), and antibodies related to: Antisera (Serum containing antibodies against an infectious organism). Pharmaceuticals could also be used.

In practice, products could be prepared for all domestic and wild species. Specifically, products could include antigens or antibodies related to the following for cattle: Infectious Bovine Rhinotracheitis (IBR) virus, Bovine Virus Diarrhea (BVD) virus, Parainfluenza 3 (PI3) virus, Bovine Respiratory Syncytial Virus (BRSV), Haemophilus, Pasteurella, Leptospira, Clostridium, Campylobacter, Corynebacterium, Escherichia, Moraxella, Salmonella, Actinomyces, Anaplasmosis, Anthrax, Brucella, Coronavirus, Rotavirus, Staphylococcus, Trichomonas, Fusobacterium.

For dogs, the following could be used: Distemper, Measles, Adenovirus, Parainfluenza, Leptospira, Bordetella, Parvovirus, Coronavirus, Borrelia, Rabies, Salmonella.

For horses, the following could be used: Anthrax, Escherichia, Ehrlichia, Encephalomyelitis, Influenza, Rabies, Rhinopneumonitis, Salmonella, Tetanus, Viral Arteritis.

For cats, the following could be used: Rhinotracheitis, Calicivirus, Panleukopenia, Leukemia, Rabies, Infectious Peritonitis, Microsporum.

For sheep, the following could be used: Clostridium, Corynebacterium, Escherichia, Pasteurella, Salmonella, Anthrax, Bacteroides, Bluetongue, Campylobacter, Chlamydia, Ecthyma, Epididymitis, Rabies, Tetanus.

For swine, the following could be used: Anthrax, Bordetella, Clostridium, Corynebacterium, Escherichia, Encephalomyocarditis, Erysipelas, Actinobacillus, Haemophilus, Leptospira, Mycoplasma, Pasteurella, PRRS, Influenza, Parvovirus, Pseudorabies, Rotavirus, Tetanus, Salmonella, Streptococcus, Servulina, Transmissible Gastroenteritis.

For avian, the following could be used: Bronchitis, Bursal Disease, Mycoplasma, Newcastle Disease, Pasteurella, Reovirus, Bordetella, Coccidiosis, Escherichia, Encephalomyelitis, Erysipelas, Fowl Pox, Haemophilus, Adenovirus, Herpesvirus, Influenza, Laryngotracheitis, Pacheco Disease, Paramyxovirus, Salmonella.

In addition, as earlier explained, the pellets, besides including the active which may be an antigen as above-described, and the colorant, they may contain other materials known in the tableting art. They may include fillers (inert), and fillers which are functional. Inert fillers include the following: Lactose, Mannitol, Dextrate, Dextrose, Fructose, Sucrose, Galactose, Maltose, Sorbitol, Dextran, Dextrin, Calcium carbonate, Calcium sulfate, Dicalcium phosphate. Functional fillers include the following: Alginic acid, Various cellulosics (Hydroxypropyl cellulose (HPC), Hydroxypropyl methylcellulose (HPMC), Oxidized cellulose (OC), Microcrystalline cellulose (MCC), Ethyl cellulose (EC), Hydroxyethyl cellulose (HEC), Methyl cellulose (MC), Carboxymethyl cellulose (CMC), Cellulose acetate (CA), Cellulose acetate butyrate (CAB), Cellulose acetate propionate (CAP), Cellulose sodium phosphate (CSP), Cellulose triacetate (CTA), Cellulose acetate phthalate (C-A-P), Hydroxypropyl methylcellulose phthalate (HPMCP), Cellulose acetate trimellitate (C-A-T), Hydroxypropyl methylcellulose acetate succinate (HPMCAS), Sodium carboxymethyl cellulose), Polyanhydrides, Polymethyl merthacrylate, Polylactides, Polyglycolides, Carbomer, Gellan gum, Sodium alginate, Acrylic copolymers, Glyceryl monostearate, Zein, Cholesterol, Agarose, Chitosan, Xanthan gum, Polyethylene glycol (PEG), Gelatin, Povidone, Natural gum. The pellets may also contain Glidants (Flow Aids), Disintegrants, Lubricants, Adjuvants, Antibiotic Preservatives, etc. Suitable Glidants include: Precipitated silica, Fumed silica. Suitable Disintegrants include: Sodium starch glycolate, Crospovidone, Croscarmellose sodium. Suitable Lubricants include: Stearic acid, Magnesium stearate, Calcium stearate, Sodium stearyl fumarate, Glyceryl monostearate, Triglyceride esters. Suitable Adjuvants include: Aluminum hydroxide, Saponin, Dimethyl dioctadecyl ammonium bromide (DDA bromide), Bacterial extracts. If antibiotics are to be included, pellets may, for example, include the following: Penicillin, Streptomycin, Gentamicin, Polymyxin B, Amphotericin B, Nystatin, Tetracycline, Neomycin.

Preferably, the inert filler is lactose, and the functional filler hydroxypropyl cellulose (3%–30% of the pellet by weight). The glidant preferred is precipitated silica (0.5% of the pellet weight). The most satisfactory lubricant used to date would be calcium stearate at 2% of the pellet weight. Adjuvants include levels from 1%–20% of the pellet weight and may be aluminum hydroxide or DDA bromide. A suitable antibiotic preservative included at a <1% of pellet weight would be gentamicin.

All of the above may also be incorporated into the payload of ballistic implants as previously explained.

What is claimed is:

1. A method of inoculating animals with a plurality of biologically active pellets comprising:
   providing an implant apparatus for implanting biologically active pellets in an animal which can be operably coupled to a dosing pellet magazine;
   said dosing pellet magazine comprising:
      a series of loaded dosing pellet see-through columns, each loaded with a plurality of dosing pellets, each pellet color-coded to represent a particular medicament; and thereafter,
   implanting the plurality of dosing pellets in an animal to be inoculated with a single injection.

2. The method of claim 1 wherein the pellets are loaded with the doses all in the same order.

3. The method of claim 1 wherein the animal selected is cattle.

4. The method of claim 1 wherein the pellet is from 3% to 30% of functional filler.

5. The method of claim 1 wherein the pellet is 0.5% by weight glidant.

6. The method of claim 1 wherein the pellet is 1%–2% lubricant.

7. The method of claim 1 wherein the pellet is from 1% to 20% adjuvant.

8. The method of claim 1 which includes the antibiotic gentamicin.

9. A dosing pellet magazine, comprising:
   a plurality of connected see through pellet dosing columns, each of said columns being loaded with a plurality of dosing pellets, with each pellet color-coded to represent a particular biologically active medicament.

10. The dosing pellet magazine of claim 9 wherein the pellets are loaded with the doses all in the same order.

11. The dosing pellet magazine of claim 9 wherein the animal selected is cattle.

12. The dosing pellet magazine of claim 9 wherein the pellet is from 3% to 30% of functional filler.

13. A system of packaging biologically active implants, comprising:
   selecting a plurality of biologically active medicaments for implant dosing;
   coloring each selected medicament with a unique color to represent the selected medicament;
   placing the medicaments in a see through pellet magazine, with the medicaments in a prearranged order;
   consistently using the same color scheme for packaging and instructional materials used with the packaged pellet implant doses.

14. The system of claim 13 wherein the pellets are loaded with the doses all in the same order.

* * * * *